United States Patent
Connor et al.

(10) Patent No.: US 6,566,425 B1
(45) Date of Patent: May 20, 2003

(54) POLYMERIC ARTICLES COMPRISING NOVEL BISMETHINE BENZODIFURANONE DERIVATIVE COLORANTS

(75) Inventors: Daniel M. Connor, Inman, SC (US); Eric B. Stephens, Roebuck, SC (US)

(73) Assignee: Milliken & Company, Spartanburg, SC (US)

( * ) Notice: Subject to any disclaimer, the term of this patent is extended or adjusted under 35 U.S.C. 154(b) by 43 days.

(21) Appl. No.: 09/955,229

(22) Filed: Sep. 18, 2001

(51) Int. Cl.$^7$ .............................. C08K 5/46; C08K 5/48; C08K 5/35
(52) U.S. Cl. .............................. 524/83; 524/95; 524/99; 524/100; 524/102; 106/287.2; 106/287.29
(58) Field of Search .............................. 524/83, 95, 99, 524/100, 102; 106/287.2, 287.24

(56) References Cited

U.S. PATENT DOCUMENTS

| | | | |
|---|---|---|---|
| 3,207,736 A | | 9/1965 | Wijga .......................... 260/93.7 |
| 4,617,374 A | * | 10/1986 | Pruett et al. ................... 528/288 |
| 4,992,204 A | * | 2/1991 | Kluger et al. ............ 252/301.16 |
| 5,665,150 A | * | 9/1997 | Schwarz .................... 106/31.43 |
| 5,779,778 A | * | 7/1998 | Gregory et al. ........... 106/31.27 |
| 6,492,533 B1 | * | 10/2002 | Connor et al. ............... 549/299 |

FOREIGN PATENT DOCUMENTS

| | | | |
|---|---|---|---|
| GB | 2 312 435 | * | 10/1997 |
| WO | WO 00/24736 | * | 5/2000 |

* cited by examiner

*Primary Examiner*—Kriellion A. Sanders
(74) *Attorney, Agent, or Firm*—Terry T. Moyer; William S. Parks

(57) ABSTRACT

Colorants comprising a chromophore having two methine moieties attached to a benzodifuranone backbone, wherein said moieties optionally have at least one poly(oxyalkylene) chain, preferably at least two such chains attached thereto are provided. Such colorants exhibit excellent thermal stability, effective colorations, excellent low extraction rates, and effective lightfastness levels, particularly when incorporated within certain media and/or on the surface of certain substrates, particularly polyesters. The optional poly (oxyalkylene) chains also increase the solubility in different solvents or resins thereby permitting the introduction of such excellent coloring chromophores within diverse media and/or on diverse substrates as well as provides a liquid colorant which facilitates handling. Compositions and articles comprising such colorants are provided as are methods for producing such inventive colorants.

45 Claims, No Drawings

POLYMERIC ARTICLES COMPRISING NOVEL BISMETHINE BENZODIFURANONE DERIVATIVE COLORANTS

FIELD OF THE INVENTION

This invention relates to colorants comprising a chromophore having two methine moieties attached to a benzodifuranone backbone, wherein said moieties optionally have at least one poly(oxyalkylene) chain, preferably at least two such chains attached thereto. Such colorants exhibit excellent thermal stability, effective colorations, excellent low extraction rates, and effective lightfastness levels, particularly when incorporated within certain media and/or on the surface of certain substrates, particularly polyesters. The optional poly(oxyalkylene) chains also increase the solubility in different solvents or resins thereby permitting the introduction of such excellent coloring chromophores within diverse media and/or on diverse substrates as well as provides a liquid colorant which facilitates handling. Compositions and articles comprising such colorants are provided as are methods for producing such inventive colorants.

DISCUSSION OF THE PRIOR ART

All U.S. patents cited within this specification are hereby incorporated by reference.

There continues to be a need to provide versatile colorants within various applications such that the coloring agent itself exhibits excellent colorations (particularly at low color loadings and due to inherently high quantum absorption efficiency), high thermal stability, effective lightfastness, low extraction (or drastic reduction in possibility of removal therefrom via extraction by solvents or like sources), ease in handling, ability to mix thoroughly with other coloring agents and thus to provide effective different hues and tints within or on target substrates, and acceptable toxicity levels. There has been a need to provide improved colorants meeting this criteria for certain thermoplastic media, such as polyesters, such that the colorants themselves exhibit excellent compatibility therein (for instance in terms of intrinsic viscosity loss and the other characteristics desired for such plastics as noted above). In particular, such characteristics for polyesters are desired for colorants that absorb, for example, though not necessarily, within the red portion of the visible spectrum. Other hues are available as well for such a desired, high-performing polyester plastic colorant, including blue, yellow, orange, and the like, all dependent on the presence of certain coupling or modifying moieties present on the chromophore backbone itself. It is believed and, as noted above, has been determined that such desirable polyester plastic colorations with the characteristics noted above are possible through the addition of certain pendant groups to the chromophore backbone which do not act as couplers or color modifiers [such as, for example poly (oxyalkylene) groups] and thus any chromophore (and resultant hue or tint) may be utilized with the desired benzodifuranone bismethine chromophore itself.

Previous coloring agents for such end-uses have included pigments, dyes, or dyestuffs, with each having its own drawback, be it an extraction problem from the finished article, a handling problem during manufacturing due to solid dust particles, a staining problem, due to the difficulty associated with cleaning such coloring agents from manufacturing machinery after colored plastic production, and other like issues. As a result, there is a clear desire to provide easier to handle, less extractable, easy-to-clean, etc., coloring agents for introduction within thermoplastic articles to provide decorative, aesthetic, and other like effects. However, the chromophores present within such dyes, pigments, and the like, are highly desired for the hues and shades they provide within the ultimate thermoplastic articles themselves. Facilitating the introduction of such chromophores within such formulations is thus a highly desired target within the colored thermoplastic industry, whether it be in terms of handling, extraction, cleaning, or the like.

Attempts to meet this desire have included the introduction of certain standard types of polymeric colorants within plastics (be they thermoplastics or thermoset types). These colorants are primarily poly(oxyalkylenated) compounds, such as triphenylmethanes, methines, and the like (i.e., those found within U.S. Patent U.S. Pat. No. 4,992,204, to Kluger et al.). Some of these colorants exhibit certain problems during incorporation into thermosets and thermoplastics. In thermoplastic compositions such as polyesters, many of these previously disclosed compositions are not stable at the polyester processing temperatures. As a result, the colorations provided by such polymeric colorants may be reduced in strength or changed in shade under such circumstances. Other types of colorants have been discussed within the prior art, such as azos and bisazos, but the specific colorations provided by such compounds are limited to certain hues and their utilization within polyesters is suspect from a number of perspectives (such as thermal stability, and the like). There is thus a desire to introduce new types of colorants comprising different types of chromophores for the purpose of providing new, effective, versatile colorants for such myriad end-uses as noted above and that exhibit excellent colorations, extraction, thermal stability, mixing with other coloring agents, and low toxicity, at least.

A certain class of colorants, namely benzodifuranone derivatives, exhibit excellent colorations and have been utilized within different applications, most prominently within inks, such as in U.S. Pat. No. 5,665,150 to Schwarz, and U.S. Pat. No. 5,779,778 to Gregory et al. and as disperse dyes for polyester, such as in *J. Soc. Dyers Colour.* 110, 1994, p, 178. The chromophores disclosed in this art are significantly structurally and thus electronically different from the inventive chromophores disclosed herein, exhibiting a substituted phenyl group attached directly to the benzodifuranone core structure, and thus cannot be classified as methines. There has also been some discussion of introducing isatin-based benzodifuranones within plastics as disclosed within published PCT Application WO00/24736 to Ciba Specialty Chemicals. Such compounds are limited to non-polymeric species and, again, require the presence of isatin as a substituent (and thus a heterocyclic pendant group attached to the double bond between such an isatin adduct and the backbone benzodifuranone compound). Apparently, such compounds provide effective colorations within plastics; however, there is no discussion of the handling issues, mixing capabilities with other colorants, migratory properties, lightfastness, or other concerns with colorants for plastics. Furthermore, the reaction with isatin is rather costly and the yield is suspect thus increasing the potential costs to the end-user and/or the consumer. A new type of benzodifuranone colorant for plastic applications (at least) is thus desirable, primarily due to the potential colorations provided by such base chromophores. Furthermore, simplified methods of producing such benzodifuranone derivatives are also desired such that the end colorant can be tailored in its constitution to any end-use application through the presence of poly(oxyalkylene) groups thereon. Such an option would thus provide much-needed versatility for such desirable coloring agents within various media (including the aforementioned plastics, liquids, foams, and the like). To date, there have been no teachings or fair suggestions of such a highly desirable, specific potentially polymeric benzodifuranone derivative colorant within the pertinent prior art or within the colorant industry itself.

DESCRIPTION OF THE INVENTION

It is thus an object of the invention to provide novel thermally stable polymeric colorants for utilization within thermoplastic and thermoset articles based on bismethine benzodifuranone backbone structures. Yet another object of this invention is to provide excellent colorations within liquid compositions (such as inks, and the like) through the utilization of the same bismethine benzodifuranone-type compounds as noted above. The features of this new chromophore are exceptionally high color strength and exceptionally high heat stability. In the liquid embodiments demonstrated herein, the colorant exhibits low extraction from thermoplastics such as polyester, little effect on the molecular weight (intrinsic viscosity) of polyester when incorporated at high color loading, low toxicity and ease of handling (homogeneous liquid). It is a further object of this invention to provide new solid dye compositions suitable for the coloration of textile materials, in particular advantageous in the dyeing of hydrophobic fibers such as polyester.

It is to be understood that the term alkyl as used throughout is intended to encompass any straight or branched alkyl moiety, having anywhere from 1 to 30 carbons therein; the same chain length applies to the term "alkoxy" as well. Also, the terms substituted phenyl and substituted polyphenyl are intended to encompass any phenyl system having any type of pendant group attached thereto, including, without limitation, alkyl groups, alkylene groups, alcohol groups, ether groups, ester groups, amine groups, nitro groups, amide groups, hydroxyls, thiols, and the like. Phenyl is basically an unsubstituted ring system (and thus includes hydrogens only as pendant groups).

The present invention preferably encompasses colorants conforming to the structure of Formula (I)

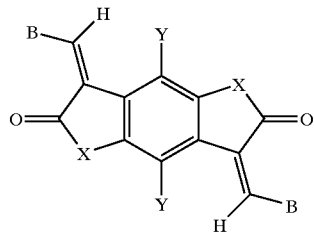

(I)

wherein Y is selected from the group consisting of hydrogen, alkyl, halogen, alkenyl, hydroxy, and alkoxy; X is selected from the group consisting of any atom that provides a heterocyclic system for the cyclic ring; B is selected from the group consisting of alkenyl, phenyl, polyphenyl, substituted phenyl, substituted polyphenyl, alkenyl-Q—A, phenyl-Q—A, polyphenyl-Q—A, substituted phenyl-Q—A, and substituted polyphenyl-Q—A, wherein Q is selected from the group consisting of N, O, S, $SO_2$, $SO_3$, $CO_2$, $SO_2N$, alkyl, and alkoxy, and A either conforms to the structure of Formula (VII)

[polyoxyalkylene constituent]$_z$R' (VII)

wherein z is 1 or 2; polyoxyalkylene constituent is selected from the group consisting of at least three monomers of at least one $C_{2-20}$ alkyleneoxy group, glydicol, glycidyl, or mixtures thereof, monomers of at least one $C_{2-20}$ alkyleneoxy group, glydicol, glycidyl, or mixtures thereof; and R' is selected from the group consisting of hydrogen, $C_{1-20}$ alkyl, $C_{1-20}$ alkylester, halo, hydroxyl, hydrogen, thio, cyano, sulfonyl, sulfo, sulfato, aryl, nitro, carboxyl, $C_{1-20}$ alkoxy, amino, $C_{1-20}$ alkylamino, acrylamino, $C_{1-20}$ alkylthio, $C_{1-20}$ $C_{1-20}$ alkylsufonyl, $C_{1-20}$ alkylphenyl, phosphonyl, $C_{1-20}$ alkylphosphonyl, $C_{1-20}$ alkoxycarbonyl, phenylthio; or conforms to the structure E, wherein E is an unsaturated heterocylic residue selected from the group consisting of furyl, thienyl, pyrrolyl, pyridyl, pyranyl, thiazolyl, oxazolyl, pyrazolyl, imidazolyl, thiadiazolyl, and s-triazoyl. Alternatively, E represents a saturated heterocyclic residue selected from the group consisting of tetrahydrofuryl, tetrahydrothienyl, pyrrolidyl, piperidyl, tetrahydropyranyl, piperazinyl, morphonyl, and hexahydroazepinyl. Also, E represents a hetrocyclic residue condensed with benzene rings such as benzofurnayl, benzothienyl, indolyl, benzoxazolyl, benzimidazolyl, and benzothiazolyl, as well as a phenyl substituted with any or all of $R_1$, $R_2$, $R_3$, $R_4$, and $R_5$. Preferably, Y is hydrogen, X is O, $R_1$, $R_2$, $R_3$, $R_4$, $R_5$, and R' are hydrogen, with preferably, though not necessarily, at least one of $R_1$, $R_2$, $R_3$, $R_4$, and $R_5$ being Q—A; polyoxyalkylene constituent is ethylene oxide (EO), propylene oxide (PO), or any combinations thereof; and Q is N. Preferably, B is a moiety that exhibits conjugation when incorporated and present within the structure (I) in order to provide desired colorations, as well as a moiety including the above-defined Q—A group; more thorough descriptions of such groups are presented below.

More specifically, and preferably (though in a non-limiting capacity), the inventive benzodifuranone bismethine colorant conforms to the structure of (II)

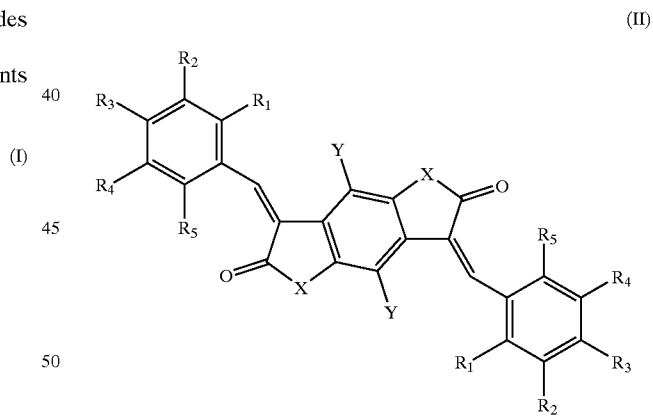

(II)

wherein X and Y are defined as for (I), above, and wherein $R_1$, $R_2$, $R_3$, $R_4$, and $R_5$ are the same or different and are selected from the group consisting of hydrogen, $C_{1-20}$ alkyl, $C_{-1-20}$ alkylester, halo, hydroxyl, hydrogen, thio, cyano, sulfonyl, sulfo, sulfato, aryl, nitro, carboxyl, $C_{1-20}$ alkoxy, amino, $C_{1-20}$ alkylamino, acrylamino, $C_{1-20}$ alkylthio, $C_{1-20}$ $C_{1-20}$ alkylsufonyl, $C_{1-20}$ alkylphenyl, phosphonyl, $C_{1-20}$ alkylphosphonyl, $C_{1-20}$ alkoxycarbonyl, phenylthio, and Q—A, wherein Q is selected from the group consisting of N, O, S, $SO_2$, $SO_3$, $CO_2$, $SO_2N$, alkyl and alkoxy, and A either conforms to the structure of Formula (VII)

[polyoxyalkylene constituent]$_z$R' (VII)

wherein z is 1 or 2; polyoxyalkylene constituent is selected from the group consisting of at least three monomers of at least one $C_{2-20}$ alkyleneoxy group, glydicol, glycidyl, or mixtures thereof, monomers of at least one $C_{2-20}$ alkyleneoxy group, glydicol, glycidyl, or mixtures thereof; and R' is selected from the group consisting of hydrogen, $C_{1-20}$ alkyl, $C_{1-20}$ alkylester, halo, hydroxyl, hydrogen, thio, cyano, sulfonyl, sulfo, sulfato, aryl, nitro, carboxyl, $C_{1-20}$ alkoxy, amino, $C_{1-20}$ alkylamino, acrylamino, $C_{1-20}$ alkylthio, $C_{1-20}$ $C_{1-20}$ alkylsufonyl, $C_{1-20}$ alkylphenyl, phosphonyl, $C_{1-20}$ alkylphosphonyl, $C_{1-20}$ alkoxycarbonyl, and phenylthio; or conforms to the structure of E, wherein E is an unsaturated heterocylic residue selected from the group consisting of furyl, thienyl, pyrrolyl, pyridyl, pyranyl, thiazolyl, oxazolyl, pyrazolyl, imidazolyl, thiadiazolyl, and s-triazoyl. Alternatively, E represents a saturated heterocyclic residue selected from the group consisting of tetrahydrofuryl, tetrahydrothienyl, pyrrolidyl, piperidyl, tetrahydropyranyl, piperazinyl, morphonyl, and hexahydroazepinyl. Also, E represents a heterocyclic residue condensed with benzene rings such as benzofurnayl, benzothienyl, indolyl, benzoxazolyl, benzimidazolyl, and benzothiazolyl, as well as a phenyl substituted with any or all of $R_1$, $R_2$, $R_3$, $R_4$, and $R_5$. Preferably, $R_1$, $R_2$, $R_3$, $R_4$, $R_5$, and R' are hydrogen, with preferably, though not necessarily, at least one of $R_1$, $R_2$, $R_3$, $R_4$, and $R_5$ being Q—A; polyoxyalkylene constituent is ethylene oxide (EO), propylene oxide (PO), or any combinations thereof; and Q is N.

Further preferred inventive colorants conform to the following structures (III), (IV), (V), and (VI):

(III)

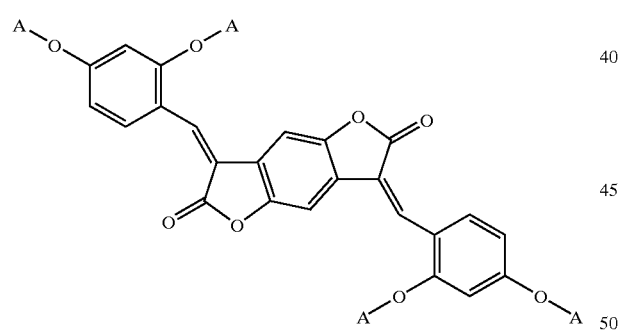

wherein A is represented by the Formula (VII)

[polyoxyalkylene constituent]$_z$R'    (VII)

wherein z is 1 or 2; polyoxyalkylene constituent is selected from the group consisting of at least three monomers of at least one $C_{2-20}$ alkyleneoxy group, glydicol, glycidyl, or mixtures thereof, monomers of at least one $C_{2-20}$ alkyleneoxy group, glydicol, glycidyl, or mixtures thereof; and R' is selected from the group consisting of hydrogen, $C_{1-20}$ alkoxy, $C_{1-20}$ alkyl, and $C_{1-20}$ esters.

(IV)

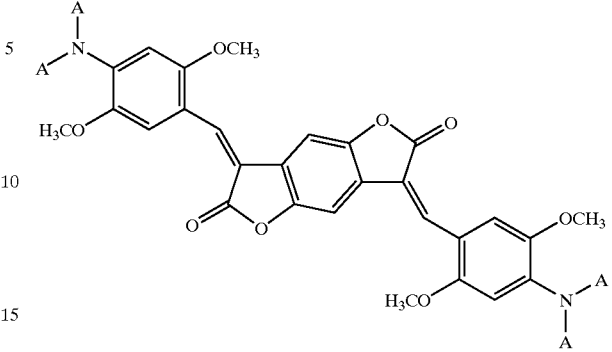

wherein A is represented by the Formula (VII)

[polyoxyalkylene constituent]$_z$R'    (VII)

wherein z is 1 or 2; polyoxyalkylene constituent is selected from the group consisting of at least three monomers of at least one $C_{1-20}$ alkyleneoxy group, glydicol, glycidyl, or mixtures thereof, monomers of at least one $C_{2-20}$ alkyleneoxy group, glydicol, glycidyl, or mixtures thereof, and R' is selected from the group consisting of hydrogen, $C_{1-20}$ alkoxy, $C_{1-20}$ alkyl, and $C_{1-20}$ esters.

(V)

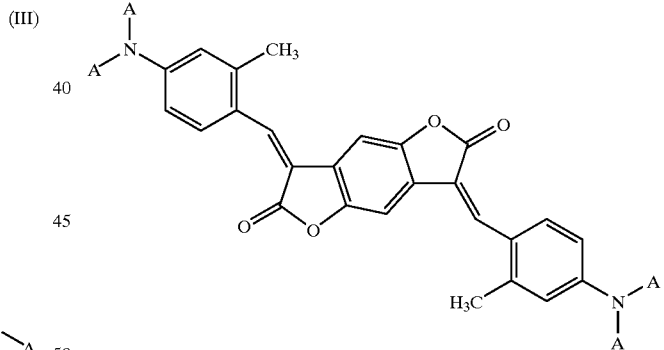

wherein A is represented by the Formula (VII)

[polyoxyalkylene constituent]$_z$R'    (VII)

wherein z is 1 or 2; polyoxyalkylene constituent is selected from the group consisting of at least three monomers of at least one $C_{2-20}$ alkyleneoxy group, glydicol, glycidyl, or mixtures thereof, monomers of at least one $C_{2-20}$ alkyleneoxy group, glydicol, glycidyl, or mixtures thereof; and R' is selected from the group consisting of hydrogen, $C_{1-20}$ alkoxy, $C_{1-20}$ alkyl, and $C_{1-20}$ esters.

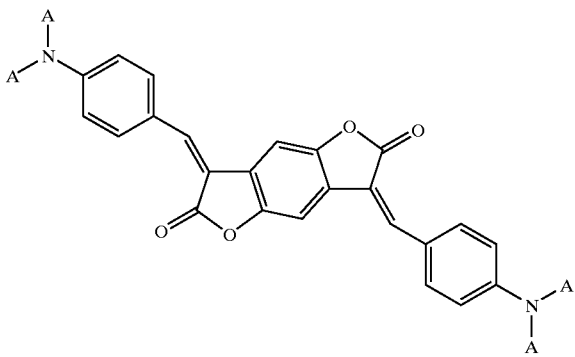

(VI)

wherein A is represented by the Formula (VII)

[polyoxyalkylene constituent]$_z$R'  (VII)

wherein z is 1 or 2; polyoxyalkylene constituent is selected from'the group consisting of at least three monomers of at least one $C_{2-20}$ alkyleneoxy group, glydicol, glycidyl, or mixtures thereof, monomers of at least one $C_{2-20}$ alkyleneoxy group, glydicol, glycidyl, or mixtures thereof, and R' is selected from the group consisting of-hydrogen, $C_{1-20}$ alkoxy, $C_{1-20}$ alkyl, and $C_{1-20}$ esters.

Compositions comprising such compounds of (I)–(VI) are also encompassed within this invention, particularly those comprising such compounds and other coloring agents, ultraviolet absorbers, bluing agents, or mixtures thereof, as liquids or as pellets for further introduction within desired molten thermoplastic or thermoset formulations (or precursor formulations). Methods of making such compositions, particularly thermoplastics, comprising such compounds of (I)–(VI) are also contemplated within this invention.

The term "thermoplastic" is intended to encompass any synthetic polymeric material that exhibits a modification in physical state from solid to liquid upon exposure to sufficiently high temperatures. Most notable of the preferred thermoplastic types of materials are polyolefins (i.e., polypropylene, polyethylene, and the like), polyester (i.e., polyethylene terephthalate, polybutylene terephthalate, polytrimethylene terephthalate, and the like), polyamides (i.e., nylon-1,1, nylon-1,2, nylon-6 or nylon-6,6), polystyrenes, polycarbonates, polyvinyl halides (i.e., polyvinyl chloride and polyvinyl difluoride, as merely examples), and the like. Preferred thermoplastics within this invention are polyesters, and most preferred is polyethylene terephthalate.

Such thermoplastic articles include bottles, storage containers, sheets, films, fibers, plaques, hoses, tubes, syringes, and the like. Included within this list would be polyester, polystyrene and other like resinous materials in sheet form which are present within windows for strength and resiliency functions. In such an instance, the inventive colorant compounds would provide or contribute to excellent colorations to such thermoplastic articles for decorative, aesthetic, and/or protective (such as ultraviolet or infrared protection) purposes. Basically, the possible uses for such a low-migratory, thermally stable colorant for such items as thermoplastics (particularly polyesters such as transparent polyethylene terephthalate) is voluminous and cannot easily be enveloped. Other possible end-uses, however, would include within solvent systems, printing inks, within and on textiles (either on or within textiles, fibers, or fabrics), within display devices such as liquid crystal displays, and the like.

The inventive colorant compounds may be added in any amount to such thermoplastics up to their saturation limits therein. Preferably, the amount is between about 0.00001 ppm to about 25,000 ppm per total amount of resin; more preferably from about 0.001 to about 15,000 ppm; still more preferably from about 0.1 to about 5,000 ppm; and most preferably from about 100 to about 2,500 ppm. Of course, the more colorant present, the darker the shade therein. When mixed with other colorants within the target thermoplastic, the same amounts would be preferred with the saturation limit dependent upon the amount of any extra colorants therein.

The term "thermoset" or "thermosets" encompasses a polymeric solid which, upon exposure to sufficient heat or in the presence of a sufficient amount of catalyst, configures itself into a pre-determined shape. Such formulations encompassed within this term includes polyurethanes, and the like. Thus, foams, sheets, articles, coverings, and the like, are all envisioned within this definition.

The inventive colorant compounds may be added in any amount to such thermosets up to their saturation limits therein. Preferably, the amount is between about 0.00001 ppm to about 25,000 ppm per total amount of resin; more preferably from about 0.001 to about 15,000 ppm; still more preferably from about 0.1 to about 5,000 ppm; and most preferably from about 100 to about 2,500 ppm. Of course, the more colorant present, the darker the shade therein. When mixed with other colorants within the target thermoset, the same amounts would be preferred with the saturation limit dependent upon the amount of any extra colorants therein.

Other types of articles contemplated within this invention for the inventive colorant compounds include, again without limitation, thermoplastic articles, such as films, sheets, bottles, containers, vials, and the like. Other colorants may be added to or incorporated therein with such inventive colorant compounds to produce different hues and tints, again for aesthetic, decorative, and/or protective purposes. Ultraviolet absorbers may also be introduced, incorporated, and the like, in order to protect the article or, if in container for, the contents therein.

Such thermoplastic and/or thermoset colorants (and other additives) are typically added to such compositions during the injection molding (or other type of molding, such as blow molding), thereof, including, and without limitation, by mixing the liquid absorber with resin pellets and melting the entire coated pellets, or through a masterbatch melting step while the resin and absorber are pre-mixed and incorporated together in pellet form. Such plastics include, again without limitation, polyolefins, polyesters, polyamides, polyurethanes, polycarbonates, and other well known resins, such as those disclosed within U.S. Pat. No. 4,640,690, to Baumgartner et al., and U.S Pat. No. 4,507,407, to Kluger et al. under the term "thermoplastics" and/or "thermosets". Generally, such plastics, including the colorant, UV absorber, and other potential additives, are formed through any number of various extrusion, etc., techniques, such as those disclosed in the aforementioned U.S. patents. Preferred thermoplastics are polyesters, such as, in one non-limiting embodiment, polyethylene terephthalate. "Plastic packaging" thus encompasses containers, sheets, blister packages, and the like, utilized for storage purposes and which include the plastics in any combination as noted above.

The term "pure, undiluted state" as used in conjunction with the inventive colorant compounds indicates that the compounds themselves without any additives are liquid at room temperature. Thus, there is no need to add solvents, viscosity modifiers, and other like additives to the compounds to effectuate such a desirable physical state.

The presence of surfactants, solvents, and the like, may be utilized to alter the solubility, coloring characteristics, and the like, of the ultimate inventive benzodifuranone bismethine colorant [whether poly(oxyalkylenated) or not] which would be understood and appreciated by the ordinarily skilled artisan within this particular art. It is also understood that solid versions of such inventive colorants (e.g., dyestuffs, pigments, and the like) could be dispersed within liquid media to provide stable dispersions thereof for further utilization.

Preferably, the colorant compounds (I)–(VI) are liquid in nature at ambient temperature and pressure and at substantial purity; however, pasty, waxy, or crystalline colorants are also encompassed within this invention. In order to effectuate coloring of substrates and media, any other standard colorant additives, such as resins, preservatives, surfactants, solvents, antistatic compounds, antioxidants, antimicrobials, and the like, may also be utilized within the inventive colorant compound compositions or methods.

For liquid composition applications, the amount present should range from about 0.00001 ppm to about 30,000 ppm of the total solvent present; preferably, from about 0.001 to about 15,000 ppm; still more preferably from about 0.1 to about 5,000 ppm; and most preferably from about 100 to about 2,500 ppm. Of course, the more colorant present, the darker the shade therein. When mixed with other colorants within the target solvent, the same amounts would be preferred.

DESCRIPTION OF THE PREFERRED EMBODIMENT

The specific formulations below, as well as the following exemplified methods of producing such and methods of coloring using such are thus indicative of the preferred embodiments of this invention (all of the initial aniline derivatives and aldehyde derivatives were produced in accordance with the method taught within U.S. Pat. No. 4,594,454 to Moore et al.):
Colorant Formation

EXAMPLE 1

To a 250 mL round bottom flask containing 33.0 g of alkoxylated (2EO 10PO 6EO) para-formyl aniline was added glycine (0.36 g), 2,5-dihydroxy-1,4-benzenediacetic acid-di-gamma-lactone [produced in accordance with the method taught within Wood et al., *Journal of the American Chemical Society*, 66, 1541 (1944)] (2.98 g), and water (25 g). The ensuing reaction mixture was placed on a rotary evaporator and mixed for approximately 5 minutes. The reaction mixture was then heated to 90–95° C. for 2.5 hours while a water aspirator vacuum was applied to the rotary evaporator. The ensuing red liquid was allowed to cool to ambient temperature overnight. Water (80 g) was then added to the product. The mixture was then stirred on the rotary evaporator and heated to 75–80° C. The mixture was then poured into a separatory funnel and allowed to phase for 30 minutes during which time two layers formed. The bottom product layer was removed and mixed with an additional 80 g of water at 75–80° C. The mixture was allowed to phase in a separatory funnel as before. The bottom product layer was then removed and stripped via rotary evaporator to give approximately 28 g of a red liquid exhibiting a $\lambda_{max}$ absorbance (in methanol) of 556 nm.

EXAMPLE 2

To a 250 mL round bottom flask containing 26.2 g of alkoxylated (10EO) aldehyde of 2,5-dimethoxyaniline was added glycine (0.35 g), 2,5-dihydroxy-1,4-benzenediacetic acid-di-gamma-lactone (4.03 g), and water (20 g). The ensuing reaction mixture was placed on a rotary evaporator and mixed for approximately 5 minutes. The reaction mixture was then heated to 90–95 C. for 2.5 hours while a water aspirator vacuum was applied to the rotary evaporator. The ensuing blue liquid was allowed to cool to ambient temperature overnight. Water (20 g) was then added to the product. The reaction mixture was then heated to 90–95 C. for 2 hours while a water aspirator vacuum was applied to the rotary evaporator to give a thick blue oil exhibiting a $\lambda_{max}$ absorbance (in methanol) of 581 nm.

EXAMPLE 3

To a 3-neck, 100 mL round bottom flask containing 30 g of alkoxylated (2EO 6PO 6EO) aldehyde of 2,5-dimethoxyaniline was added glycine (0.21 g), 2,5-dihydroxy-1,4-benzenediacetic acid-di-gamma-lactone (3.23 g), and water (10 g). The ensuing reaction mixture was heated to 80–85° C. for 4 hours. The ensuing blue liquid was allowed to cool to ambient temperature and stir overnight. The mixture was then transferred to a 1-neck 250 mL round bottom flask and stripped on a rotoary evaporator for 2 hours at 90–95° C. Water (90 g) was then added to the product. The solution was mixed and heated to 80° C. before being poured into a separatory funnel. The solution was allowed to phase separate. The bottom product layer was drained and was again washed as above with 90 g of water. The ensuing product layer was stripped via rotary evaporator to give 26 g of a blue oil exhibiting a $\lambda_{max}$ absorbance (in methanol) of 577 nm.

EXAMPLE 4

To a 3-neck, 100 mL round bottom flask containing 47.5 g of alkoxylated (2EO 6PO 6EO) aldehyde of aniline was added glycine (0.21 g), 2,5-dihydroxy-1,4-benzenediacetic acid-di-gamma-lactone (5.5 g), and water (10 g). The ensuing reaction mixture was heated to 75 C. for 3 hours. The ensuing red liquid was allowed to cool to ambient temperature and stir overnight. Water (100 g) was then added to the product. The solution was mixed and heated to 80 C. before being poured into a separatory funnel. The solution was allowed to phase separate. The bottom product layer was drained and was washed again twice as above with 100 g of water. The ensuing product layer was stripped via rotary evaporator to give 43 g of a red oil exhibiting a $\lambda_{max}$ absorbance (in methanol) of 556 nm.

EXAMPLE 5

To a 3-neck, 100 mL round bottom flask containing 70.8 g of alkoxylated (2EO 4PO 4EO) aldehyde of aniline was added glycine (0.5 g), 2,5-dihydroxy-1,4-benzenediacetic acid-di-gamma-lactone (10.5 g), and water (55 g). The ensuing reaction mixture was heated to 75 C. for 3 hours. The ensuing red liquid was allowed to cool to ambient temperature and stir overnight. Water (185 g) was then added to the product. The solution was mixed and heated to 75 C. before being poured into a separatory funnel. The solution was allowed to phase separate. The bottom product layer was drained and washed again as above with 185 g of water. The ensuing product layer was stripped via rotary evaporator to give 56 g of a red oil exhibiting a $\lambda_{max}$ absorbance (in methanol) of 554 nm.

EXAMPLE 6

To a 1-neck, 100 mL round bottom flask containing 55.1 g of alkoxylated (16EO 10PO) aldehyde of m-toluidine was added glycine (0.4 g), 2,5-dihydroxy-1,4-benzenediacetic acid-di-gamma-lactone (2.43 g), and methanol (5 mL). The ensuing reaction mixture was placed on a rotovap and stripped at >90 C. for 6 hours to give a violet oil exhibiting a $\lambda_{max}$ absorbance (in methanol) of 553 nm.

EXAMPLE 7

To a 50 mL round bottom flask containing 15.5 g of alkoxylated (8EO) aldehyde of resorcinol was added glycine (0.16 g), 2,5-dihydroxy-1,4-benzenediacetic acid-di-gamma-lactone (3.0 g), and water (20 g). The ensuing reaction mixture was placed on a rotary evaporator and mixed for approximately 5 minutes. The reaction mixture was then heated to 90–95 C. for 4 hours while a water aspirator vacuum was applied to the rotary evaporator to give a thick brown oil exhibiting a $\lambda_{max}$ absorbance (in methanol) of 468 nm.

EXAMPLE 8

To a 250 mL round bottom flask containing 29.2 g of alkoxylated (2EO/10PO/6EO) aldehyde of meta toluidine was added glycine (0.2 g), 2,5-dihydroxy-1,4-benzenediacetic acid-di-gamma-lactone (2.6 g), and water (25 g). The ensuing reaction mixture was placed on a rotary evaporator and mixed for approximately 5 minutes. The reaction mixture was then heated to 90–95 C. for 5 hours while a water aspirator vacuum was applied to the rotary evaporator to give a thick violet oil. Max. Abs (MeOH) 553 nm. Water (75 g) was added to the oil and the ensuing mixture heated to 80C. The mixture was allowed to phase and the bottom product layer separated. The product layer was washed two additional times as above. The residual water was removed via rotary evaporator to give 20 g of a violet oil $\lambda_{max}$ absorbance (in methanol) of 554 nm.

EXAMPLE 9

To a 250-ml 3-neck round bottom flask equipped with a Dean-Stark trap and a reflux condenser, were charged 2,5-dihydroxy-1,4-benzenediacetic acid-di-gamma-lactone (5 g, 30 mmol), p-dimethylamino benzaldehyde (4.5 g, 30 mmol), toluene (80 ml), piperidine (0.3 ml) and benzoic acid (0.3 g). The mixture was refluxed under nitrogen gas for 4 hours. Upon cooling to room temperature, the precipitate formed was collected by filtration and washed with toluene and acetone. After boiling with 100 ml of MeOH, the solid was collected via hot filtration and washed 3 times with 50 ml of fresh MeOH, and dried in 70 C. oven. A total of 7 g (84% yield) of product was obtained as a dark red solid exhibiting a $\lambda_{max}$ absorbance (in DMSO) of 561 nm.

Thermoplastic Composition Formation in Polyester

In each instance noted below, the sample liquid colorant was introduced within an injection molding operation for a polyester thermoplastic, in this instance polyethylene terephthalate (ClearTuf® 8006 PET resin from Shell). The liquid colorant, in an amount of 1,500 ppm of the total amount of resin, was blended via agitation onto the hot, dried polyethylene terephthalate resin (in pellet form). The blend of colorant and pellets was gravity fed into the feed throat of the machine. In the feed section, melting was accomplished through the utilization of a heated (heat transferred from the barrel of the machine) screw extruder which rotated. The rotation of the screw provided thorough mixing of the colorant and molten resin together producing a uniform plastic melt which was injected into a mold in order to form the thermoplastic article, for instance a 2 inch by 3 inch plaque with a uniform thickness of 50 mils and a surface area of 12.5 in$^2$.

This method was followed for the production of PET plaques comprising the colorants of Examples 1 and 5, above, and provided a pleasing red shade with no visible color differences, bubbles, streaks, or other deleterious effects in both sample plaques.

The same thermoplastic production method was followed for the colorant of Examples 2 and 3, above, and provided a pleasing blue shade with no visible color differences, bubbles, streaks, or other deleterious effects in both sample plaques.

The same thermoplastic production method was followed for the colorant of Example 6, above, and provided a pleasing violet shade with no visible color differences, bubbles, streaks, or other deleterious effects.

Thermoplastic Composition Formation in Polyolefin

In each instance noted below, the liquid colorant was introduced within an injection molding operation for a polyolefin thermoplastic, for instance polypropylene. Fina 7525 MZ random copolymer polypropylene was used. The liquid colorant, in an amount of 1,000 ppm of the total amount of the resin, was blended via agitation onto the resin (in pellet form). The blend of colorant and pellets was gravity fed into the feed throat of the machine. In the feed section, melting was accomplished through the utilization of a heated (heat transferred from the barrel of the machine) screw extruder which rotated. The rotation of the screw provided thorough mixing of the colorant and molten resin together producing a uniform plastic melt which was injected into a mold in order to form the thermoplastic article, for instance a 2 inch by 3 inch plaque with a uniform thickness of 50 mils and a surface area of 12.5 in$^2$.

This method was followed for the production of polypropylene plaques comprising colorant of Example 3, above, and provided a pleasing blue shade with no visible color differences, bubbles, streaks, or other deleterious effects in both samples plaques.

The same thermoplastic production method was followed for the colorant of Example 4, above, and provided a pleasing red shade with no visible color differences, bubbles, streaks, or other deleterious effects.

The same thermoplastic production method was followed for the colorant of Example 8, above, and provided a pleasing violet shade with no visible color differences, bubbles, streaks, or other deleterious effects.

Extraction Analyses for Inventive Colored Plastics a) PET Plaques

The plaques made above were tested for extraction of color under the following procedure (having a detection limit of 10 ppb) (hereinafter referred to as the "heated alcohol extraction test"):

Eight plaques were cut in half and placed in a stainless steel extraction vessel. To the extraction vessel was added 125 g of 10% ethanol (preheated to 70° C.) was added. The vessels were sealed and then placed in a 70° C. oven for 2.5 hours. The vessels were then removed and allowed to cool to room temperature. In all cases, the plaques were separated with small glass slides and were completely immersed and exposed to the extraction solvent. This test was then duplicated for the same sample.

The extracts were then analyzed spectrophotometrically to determine the presence or absence of extracted colorant. A Beckman® DU 650 spectrophotometer with a 10.0 cm path length cell was used. The instrument was first zeroed using the extract obtained from the uncolored polyester plaques. The extract from the extraction of the plaques containing the various colorant additives was then scanned through the ultraviolet/visible range to determine the presence or absence of detectable peaks at the additives' lambda max.

TABLE 1

Extraction data for Inventive Colored PET Resins

| Colorant | Result |
| --- | --- |
| From Example 5 | undetectable for both samples | b) Polypropylene Plaques

The plaques from above were subjected to the heated alcohol extraction test in duplicate. The extracts were analyzed spectrophotometrically to determine the presence or absence of extracted colorant. A Beckman® DU 650 spectrophotometer with a 1.0 cm path length cell was used. The instrument was first zeroed using the extract obtained from the uncolored polyester plaques. The extract from the extraction of the plaques containing the various colorant additives was then scanned through the ultraviolet/visible range to determine the presence or absence of detectable peaks at the additives' lambda max.

TABLE 2

Extraction Data for Inventive Polypropylene Resins

| Colorant | Result |
| --- | --- |
| From Example 3 | undetectable for both samples |
| From Example 4 | undetectable for both samples |
| From Example 8 | undetectable for both samples |

Thermal Stability Analyses of Inventive Colored Resins a) Polyester

Thermoplastic plaques (2 inches by 3 inches) of polyester terephthalate (as above) were first injection molded. A total of ten plaques were then collected from the standard injection molding operation. The same injection molding machine used to produce these first ten plaques was then was paused during production of ten further plaques and allowed to remain idle for 15 minutes at the standard polyester processing temperatures (~277° C.). At the end of the 15-minute pause, the machine was then restarted without purging the colored resin from the heated barrel of the machine. Ten consecutive plaques were then collected and numbered after resumption of the injection molding operation.

The color of the ten plaques collected from the standard operation was measured in both reflectance and transmittance on a Gretag-Macbeth Color-Eye 7000A Spectrophotometer and averaged together to represent the standard. Each of the ten consecutive plaques collected after the 15-minute hold period were measured individually and sequentially on the spectrophotometer. The color difference between the standard and the each of the ten plaques was determined by the $\Delta E_{CMC}$. The maximum $\Delta E_{CMC}$ of the ten plaques collected after the 15-minute hold period represents the largest color difference and is determined to be the colorant's thermal stability. The results are tabulated below:

TABLE 3

Thermal Stability Data in PET

| Colorant Composition | $\Delta E_{CMC}$ |
| --- | --- |
| Example 1 | 1.0 |
| Example 2 | 1.2 |
| Example 3 | 0.8 |
| Example 6 | 3.1 |

A $\Delta E_{CMC}$ of less than 4 is considered to be acceptable when analyzed by this protocol.

b) Polyolefin

The liquid colorant was introduced within an injection molding operation for a polyolefin thermoplastic, for instance polypropylene. The liquid colorant was blended via agitation onto polypropylene resin (in pellet form). The blend of colorant and pellets was gravity fed into the feed throat of the machine. In the feed section, melting was accomplished through the utilization of a heated (heat transferred from the barrel of the machine) screw extruder which rotated. The rotation of the screw provided thorough mixing of the colorant and molten resin together producing a uniform plastic melt which was injected into a mold in order to form the thermoplastic article, for instance a 2 inch by 3 inch plaque with a uniform thickness of 50 mils.

Ten plaques were collected from the injection molding operation at the standard polyolefin processing temperatures (210° C.). The injection molding machine was stopped and the processing temperatures were increased 50° C. When the injection molding machine had reached the desired temperature, the material in the barrel of the machine was purged from the barrel. The machine was stopped and remained idle for 10 minutes, while the barrel was full of the material being tested. At the end of the 10-minute period, the injection molding machine was restarted without purging the colored resin from the heated barrel of the machine. Five consecutive plaques were collected and numbered after resumption of the injection molding operation.

The color of the ten plaques collected from the standard operation was measured in both reflectance and transmittance on a Gretag-Macbeth Color-Eye 7000A Spectrophotometer and averaged together to represent the standard. Each of the five consecutive plaques collected after the 10-minute hold period were measured individually and sequentially on the spectrophotometer. The color difference between the standard and each of the five plaques was determined by the $\Delta E_{CMC}$. The maximum $\Delta E_{CMC}$ of the five plaques collected after the 10-minute hold period represents the largest color difference and is determined to be the colorant's thermal stability. The results are tabulated below:

TABLE 4

Thermal Stability Data in Propylene

| Colorant Composition | $\Delta E_{CMC}$ |
| --- | --- |
| Example 3 | 1.5 |
| Example 4 | 2.5 |
| Example 8 | 1.3 |

A $\Delta E_{CMC}$ of less than 4 is considered to be excellent when examined by this protocol.

Intrinsic Viscosity Analyses of Inventive Colorants

The sample colorant was introduced within a mixing operation for a polyester thermoplastic, for instance polyethylene terephthalate (as above). The mixing step was accomplished by the use of a C.W. Brabender Electronic Plasti-Corder®, model number EPL-V5501, torque rheometer with a Type Six 2-piece mixer attachment. Cam style removable blades were used in the mixer attachment providing a medium shear-rate mixing. The temperature of the mixing chamber was set to 285° C. and controlled via electric heating and air cooling.

The liquid colorant was weighed into a small disposable syringe. The loading of the liquid colorant was determined and adjusted based on the strength of the colorant. The hot, dried polyethylene terephthalate resin, specifically M & G ClearTuf® 8006, in pellet form, was quickly weighed into a glass jar and sealed to minimize the adsorption of moisture by the resin. The torque rheometer mixing blades were turned on and set to a speed of 25 rpm as indicated by the digital display. A 25 ft³/h flow of dried nitrogen gas was introduced into the mixing chamber through the loading ram.

The dried polyethylene terephthalate resin was then poured into the mixing chamber and the loading ram was closed while the nitrogen gas continued to flow into the chamber. Simultaneously, a stopwatch was then started to mark the beginning of the operation. After 1 minute and 30 seconds of mixing, the loading ram was raised and the liquid colorant was dispensed into the molten polyester resin. The loading ram was lowered and the liquid colorant was allowed to mix with the molten polyester resin for an additional 1 minute and 30 seconds.

After such time, the blades were then stopped and the loading ram was raised. The blades were reversed and a metal spatula was used to remove a sample of the molten, colored polyester from the mixing chamber. This molten sample was immediately compressed between two metal plates and allowed to cool to form the final thermoplastic disk.

The intrinsic viscosity of the colored thermoplastic disk was measured according to ASTM D4603. The intrinsic viscosity of the colored thermoplastic disk was compared to the intrinsic viscosity of an uncolored thermoplastic control disk, via the formula:

$$\text{IV LOSS}_{COLOR} = \text{IV}_{UNCOLORED\ CONTROL} - \text{IV}_{COLORED\ DISK}$$

The colored thermoplastic control disk was processed in the same manner as described above but without the addition of the liquid colorant. The following table reflects these measurements:

TABLE 5

IV Performance Data for Colorant in Example 1

| Loading (ppm) | IV Loss |
|---|---|
| 124 | 0.00 |
| 474 | 0.00 |
| 1594 | 0.01 |

This data indicates that the inventive color compositions have little effect on the polyester molecular weight even when incorporated at amounts to produce deep shades.

Other Plastic Applications for the Inventive Colorants a) Polyurethane

The colorant from example 1, above, was used to make a polyurethane foam according to the procedure of Example 1 in U.S. Pat. No. 5,731,398 to Milliken & Company. The finished foam product exhibited a pleasing red shade.

The same polyurethane production method was followed for the colorant of Example 2, above, and provided a pleasing blue shade.

The same thermoplastic production method was followed for the colorant of Example 8 above, and provided a pleasing violet shade.

Polyester Fabrics

The colorant from example 9 was finely powdered in a mortar and pestle and then used as a disperse dye to color polyester fabric. The dye (1.0 g) was mixed with a leveling agent (5.0 mL) (Millex™ DA-50, from ABCO), a sequestering agent (Trilon® BX, from BASF) (1.0 mL), acetic acid (4.5 mL) and water (ca. 500 mL) in a pressure vessel. A 6"×12" piece of polyester fabric was added and the mixture heated with agitation to 280° F. for 30 minutes. The fabric exhibited a pleasing red shade after rinsing.

While specific features of the invention have been described, it will be understood, of course, that the invention is not limited to any particular configuration or practice since modification may well be made and other embodiments of the principals of the invention will no doubt occur to those skilled in the art to which the invention pertains. Therefore, it is contemplated by the appended claims to cover any such modifications that incorporate the features of the invention within the true meaning, spirit, and scope of such claims.

We claim:

1. An article comprising at least one polymeric formulation selected from the group consisting of at least one thermoplastic component, at least one thermoset component, and any mixtures thereof, and also comprising at least one bismethine benzodifuranone derivative colorant, either present within said polymeric formulation or adhered to the surface of said polymeric formulation.

2. The article of claim 1 wherein said polymeric formulation is at least one thermoplastic component.

3. The article of claim 2 wherein said at least thermoplastic component is selected from the group consisting of at least one polyester, at least one polyolefin, and any mixtures thereof.

4. The article of claim 3 wherein said thermoplastic component is at least one polyester.

5. The article of claim 4 wherein said at least one polyester comprises at least polyethylene terephthalate.

6. The article of claim 3 wherein said thermoplastic component is at least one polyolefin.

7. The article of claim 6 wherein said at least one polyolefin is polypropylene.

8. The article of claim 1 wherein said polymeric formulation is at least one thermoset.

9. The article of claim 8 wherein said at least one thermoset comprises at least one polyurethane.

10. The article of claim 1 wherein said at least one bismethine benzodifuranone derivative colorant conforms to the-structure of (I)

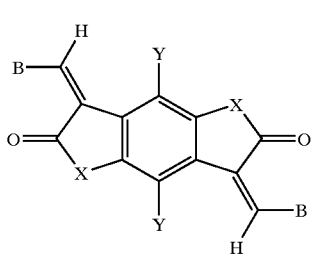

(I)

wherein Y is selected from the group consisting of hydrogen, alkyl, halogen, alkenyl, hydroxy, and alkoxy; X is oxygen; B is selected from the group consisting of alkenyl, phenyl, polyphenyl, substituted phenyl, substituted polyphenyl, alkenyl-Q—A, phenyl-Q—A, polyphenyl-Q—A, substituted phenyl-Q—A, and substituted polyphenyl-Q—A, wherein Q is selected from the group consisting of N, O, S, $SO_2$, $SO_3$, $CO_2$, $SO_2N$, alkyl, and alkoxy, and A either conforms to the stricture of Formula (VII)

$$[\text{polyoxyalkylene constituent}]_z R' \qquad (VII)$$

wherein z is 1 or 2; polyoxyalkylene constituent is selected from the group consisting of at least three monomers of at least one $C_{2-20}$ alkyleneoxy group, glydicol, glycidyl, or mixtures thereof, monomers of at least one $C_{2-20}$ alkyleneoxy group, glydicol, glycidyl, or mixtures thereof, and R' is selected from the group consisting of hydrogen, $C_{1-20}$ alkyl, $C_{1-20}$ alkylester, halo, hydroxyl, hydrogen, thio, cyano, sulfonyl, sulfo, sulfato, aryl, nitro, carboxyl, $C_{1-20}$ alkoxy, amino, $C_{1-20}$ alkylamino, acrylamino, $C_{1-20}$ alkylthio, $C_{1-20}$ $C_{1-20}$ alkylsufonyl, $C_{1-20}$ alkylphenyl, phosphonyl, $C_{1-20}$ alkylphosphonyl, $C_{1-20}$ alkoxycarbonyl, phenylthio; or conforms to the structure E, wherein E is an unsaturated heterocylic residue selected from the group consisting of furyl, thienyl, pyrrolyl, pyridyl, pyranyl, thiazolyl, oxazolyl, pyrazolyl, imidazolyl, thiadiazolyl, and s-triazoyl.

11. The article of claim 10 wherein said polymeric formulation comprises at least one thermoplastic component.

12. The article of claim 11 wherein said at least one thermoplastic component comprises at least one polyester.

13. The article of claim 12 wherein said polyester comprises at least polyethylene terephthalate.

14. The article of claim 11 wherein said thermoplastic component comprises at least one polyolefin.

15. The article of claim 14 wherein said at least one polyolefin comprises at least one polypropylene.

16. The article of claim 1 wherein said at least one bismethine benzodifuranone derivative colorant conforms to the structure of (II)

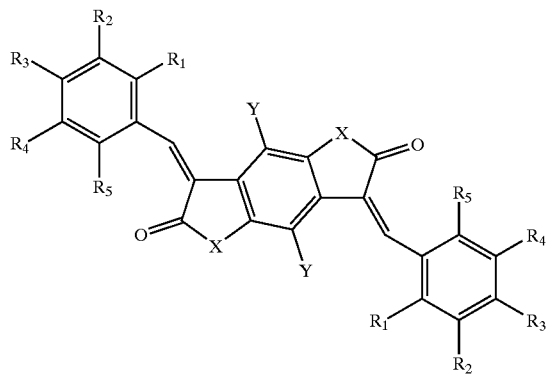

(II)

wherein Y is selected from the group consisting of hydrogen, alkyl, halogen, alkenyl, hydroxy, and alkoxy; X is oxygen; and wherein $R_1$, $R_2$, $R_3$, $R_4$, and $R_5$ are the same or different and are selected from the group consisting of hydrogen, $C_{1-20}$ alkyl, $C_{1-20}$ alkylester, halo, hydroxyl, hydrogen, thio, cyano, sulfonyl, sulfo, sulfato, aryl, nitro, carboxyl, $C_{1-20}$ alkoxy, amino, $C_{1-20}$ alkylamino, acrylamino, $C_{1-20}$ alkylthio, $C_{1-20}$ $C_{1-20}$ alkylsulfonyl, $C_{1-20}$ alkylphenyl, phosphonyl, $C_{1-20}$ alkylphosphonyl, $C_{1-20}$ alkoxycarbonyl, phenylthio, and Q—A, wherein Q is selected from the group consisting of N, O, S, $SO_2$, $SO_3$, $CO_2$, $SO_2N$, alkyl, and alkoxy, and A either conforms to the structure of Formula (VII)

$$[\text{polyoxyalkylene constituent}]_z R' \qquad (VII)$$

wherein z is 1 or 2; polyoxyalkylene constituent is selected from the group consisting of at least three monomers of at least one $C_{2-20}$ alkyleneoxy group, glydicol, glycidyl, or mixtures thereof, monomers of at least one $C_{2-20}$ alkyleneoxy group, glydicol, glycidyl, or mixtures thereof, and R' is selected from the group consisting of hydrogen, $C_{1-20}$ alkyl, $C_{1-20}$ alkylester, halo, hydroxyl, hydrogen, thio, cyano, sulfonyl, sulfo, sulfato, aryl, nitro, carboxyl, $C_{1-20}$ alkoxy, amino, $C_{1-20}$ alkylamino, acrylamino, $C_{1-20}$ alkylthio, $C_{1-20}$ $C_{1-20}$ alkylsufonyl, $C_{1-20}$ alkylphenyl, phosphonyl, $C_{1-20}$ alkylphosphonyl, $C_{1-20}$ alkoxycarbonyl, and phenylthio; or conforms to the structure of E, wherein E is an unsaturated heterocylic residue selected from the group consisting of furyl, thienyl, pyrrolyl, pyridyl, pyranyl, thiazolyl, oxazolyl, pyrazolyl, imidazolyl, thiadiazolyl, and s-triazoyl.

17. The article of claim 16 wherein said polymeric formulation comprises at least one thermoplastic component.

18. The article of claim 17 wherein said at least one thermoplastic component comprises at least one polyester.

19. The article of claim 18 wherein said polyester comprises at least polyethylene terephthalate.

20. The article of claim 17 wherein said thermoplastic component comprises at least one polyolefin.

21. The article of claim 20 wherein said at least one polyolefin comprises at least one polypropylene.

22. The article of claim 1 wherein said bismethine benzodifuranone derivative colorant conforms to the structure of (III)

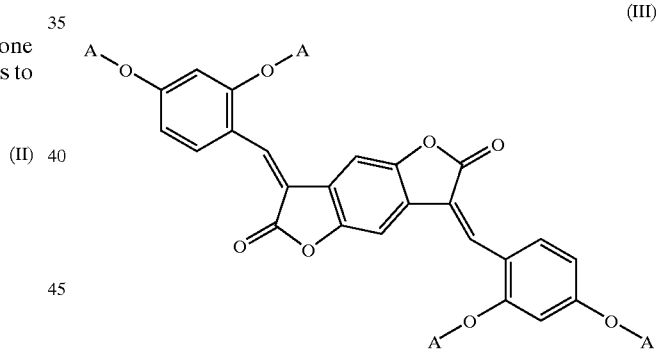

(III)

wherein A is represented by the Formula (VII)

$$[\text{polyoxyalkylene constituent}]_z R' \qquad (VII)$$

wherein z is 1 or 2; polyoxyalkylene constituent is selected from the group consisting of at least three monomers of at least one $C_{2-20}$ alkyleneoxy group, glydicol, glycidyl, or mixtures thereof, monomers of at least one $C_{2-20}$ alkyleneoxy group, glydicol, glycidyl, or mixtures thereof, and R' is selected from the group consisting of hydrogen, $C_{1-20}$ alkoxy, $C_{1-20}$ alkyl, and $C_{1-20}$ esters.

23. The article of claim 22 wherein said polymeric formulation comprises at least one thermoplastic component.

24. The article of claim 23 wherein said at least one thermoplastic component comprises at least one polyester.

25. The article of claim 24 wherein said polyester comprises at least polyethylene terephthalate.

26. The article of claim 23 wherein said thermoplastic component comprises at least one polyolefin.

27. The article of claim 26 wherein said at least one polyolefin comprises at least one polypropylene.

28. The article of claim 1 wherein said bismethine benzodifuranone derivative colorant conforms to the structure of (IV)

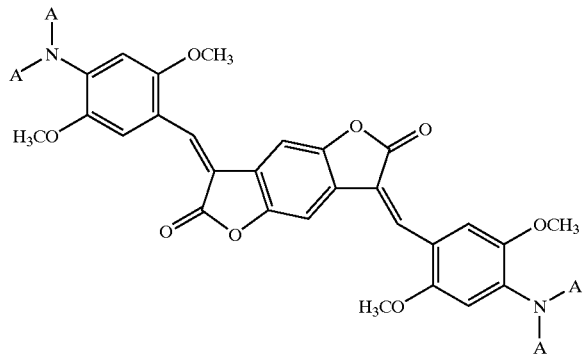

(IV)

wherein A is represented by the Formula (VII)

[polyoxyalkylene constituent]$_z$R'  (VII)

wherein z is 1 or 2; polyoxyalkylene constituent is selected from the group consisting of at least three monomers of at least one $C_{2-20}$ alkyleneoxy group, glydicol, glycidyl, or mixtures thereof, monomers of at least one $C_{2-20}$ alkyleneoxy group, glydicol, glycidyl, or mixtures thereof, and R' is selected from the group consisting of hydrogen, $C_{1-20}$ alkoxy, $C_{1-20}$ alkyl, and $C_{1-20}$ esters.

29. The article of claim 28 wherein said polymeric formulation comprises at least one thermoplastic component.

30. The article of claim 29 wherein said at least one thermoplastic component comprises at least one polyester.

31. The article of claim 30 wherein said polyester comprises at least polyethylene terephthalate.

32. The article of claim 29 wherein said thermoplastic component comprises at least one polyolefin.

33. The article of claim 32 wherein said at least one polyolefin comprises at least one polypropylene.

34. The article of claim 1 wherein said at least one bismethine benzodifuranone derivative colorant conforms to the structure of (V)

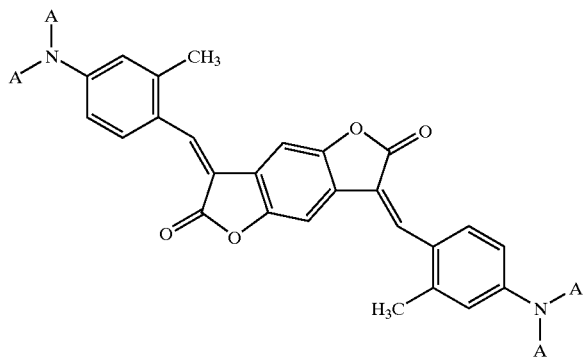

wherein A is represented by the Formula (VII)

[polyoxyalkylene constituent]$_z$R'  (VII)

wherein z is 1 or 2; polyoxyalkylene constituent is selected from the group consisting of at least three monomers of at least one $C_{2-20}$ alkyleneoxy group, glydicol, glycidyl, or mixtures thereof, monomers of at least one $C_{2-20}$ alkyleneoxy group, glydicol, glycidyl, or mixtures thereof, and R' is selected from the group consisting of hydrogen, $C_{1-20}$ alkoxy, $C_{1-20}$ alkyl, and $C_{1-20}$ esters.

35. The article of claim 34 wherein said polymeric formulation comprises at least one thermoplastic component.

36. The article of claim 35 wherein said at least one thermoplastic component comprises at least one polyester.

37. The article of claim 36 wherein said polyester comprises at least polyethylene terephthalate.

38. The article of claim 35 wherein said thermoplastic component comprises at least one polyolefin.

39. The article of claim 38 wherein said at least one polyolefin comprises at least one polypropylene.

40. The article of claim 1 wherein said at least one bismethine benzodifuranone derivative colorant conforms to the structure of (VI)

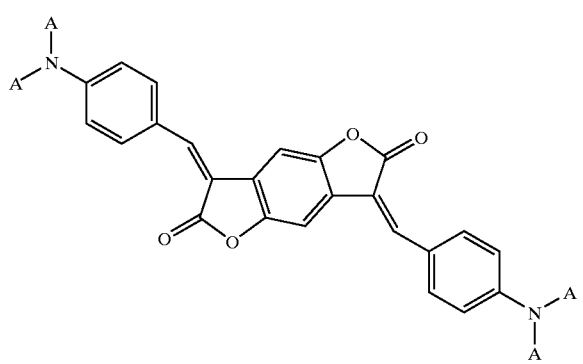

(VI)

wherein A is represented by the Formula (VII)

[polyoxyalkylene constituent]$_z$R'  (VII)

wherein z is 1 or 2; polyoxyalkylene constituent is selected from the group consisting of at least three monomers of at least one $C_{2-20}$ alkyleneoxy group, glydicol, glycidyl, or mixtures thereof, monomers of at least one $C_{2-20}$ alkyleneoxy group, glydicol, glycidyl, or mixtures thereof, and R' is selected from the group consisting of hydrogen, $C_{1-20}$ alkoxy, $C_{1-20}$ alkyl, and $C_{1-20}$ esters.

41. The article of claim 40 wherein said polymeric formulation comprises at least one thermoplastic component.

42. The article of claim 41 wherein said at least one thermoplastic component comprises at least one polyester.

43. The article of claim 42 wherein said polyester comprises at least polyethylene terephthalate.

44. The article of claim 41 wherein said thermoplastic component comprises at least one polyolefin.

45. The article of claim 44 wherein said at least one polyolefin comprises at least one polypropylene.

* * * * *